United States Patent [19]
Dowlatshahi

[11] Patent Number: 5,853,366
[45] Date of Patent: Dec. 29, 1998

[54] MARKER ELEMENT FOR INTERSTITIAL TREATMENT AND LOCALIZING DEVICE AND METHOD USING SAME

[75] Inventor: Kambiz Dowlatshahi, Chicago, Ill.

[73] Assignee: Kelsey, Inc., Chicago, Ill.

[21] Appl. No.: 676,972

[22] Filed: Jul. 8, 1996

[51] Int. Cl.[6] .................................................. A61B 17/00
[52] U.S. Cl. .......................................... 600/434; 606/116
[58] Field of Search ................................ 128/653.1, 630, 128/654, 898, 897, 657; 604/164, 264, 93; 356/247; 606/116, 130, 185, 117; 378/204, 205, 163, 20; 600/407, 300, 420, 434

[56] References Cited

U.S. PATENT DOCUMENTS

| | | | |
|---|---|---|---|
| Re. 34,936 | 5/1995 | Campbell et al. | 606/117 |
| 4,616,656 | 10/1986 | Nicholson et al. | |
| 4,774,948 | 10/1988 | Markham . | |
| 4,931,059 | 6/1990 | Markham . | |
| 5,002,548 | 3/1991 | Campbell et al. | 606/116 |
| 5,059,197 | 10/1991 | Urie et al. | |
| 5,127,916 | 7/1992 | Spencer et al. | |
| 5,158,084 | 10/1992 | Ghiatas . | |
| 5,178,164 | 1/1993 | Allen | 128/898 |
| 5,195,526 | 3/1993 | Michelson . | |
| 5,222,953 | 6/1993 | Dowlatshahi . | |
| 5,234,426 | 8/1993 | Rank et al. | |
| 5,396,897 | 3/1995 | Jain et al. | |
| 5,575,794 | 11/1996 | Walus et al. | 606/116 |
| 5,636,255 | 6/1997 | Ellis | 378/20 |

*Primary Examiner*—Marvin M. Lateef
*Assistant Examiner*—Eleni Mantis Mercader
*Attorney, Agent, or Firm*—Bell, Boyd & Lloyd

[57] ABSTRACT

A marker element is made of radiopaque material and includes at least two leg portions of approximately equal length connected at an angle relative to each other to form a generally V-shaped resilient member that is capable of being positioned wholly within the body of a patient. A localizing device and method using the marker element for marking a tissue mass of interest are also provided. The device and method include an elongate guide member, such as a cannula, having a first end that is inserted into the body so as to be directed toward a position proximate the tissue mass of interest and an opposite second end that extends from the body. A guide path extends between the first end and the second end of the guide member. The marker element is introduced into the second end of the guide member using a marker element dispenser and then urged along the guide path using a stylet or similar prodding member. The marker element collapses to a reduced size while being urged along the guide path, and substantially resumes its original V-shape upon discharge from the guide member so as to remain in a fixed position wholly within the body without irritating or traumatizing the surrounding tissue. A plurality of marker elements may be positioned in a similar manner to mark the tissue mass of interest.

20 Claims, 4 Drawing Sheets

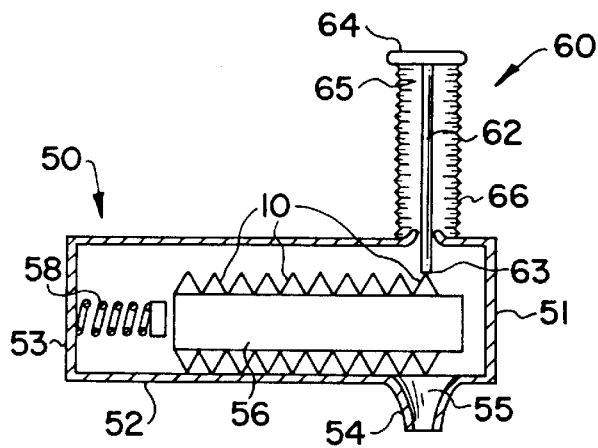 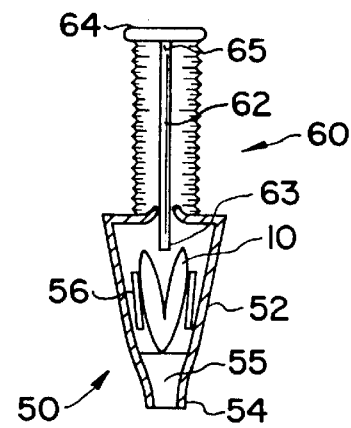
FIG. 6A          FIG. 6B
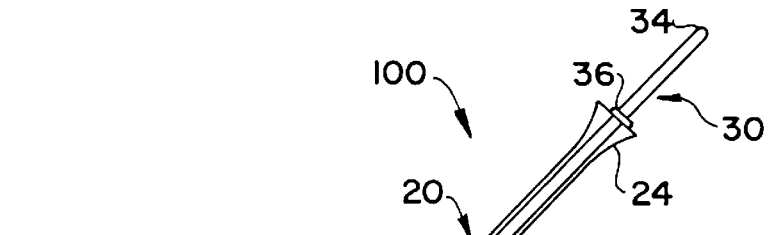
FIG. 7A
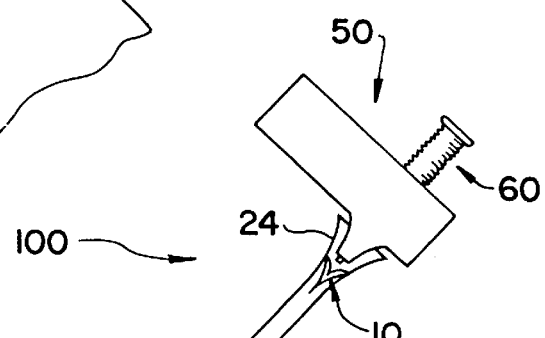
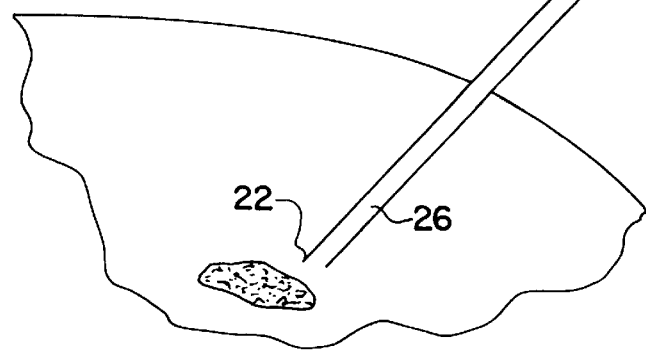
FIG. 7B

MARKER ELEMENT FOR INTERSTITIAL TREATMENT AND LOCALIZING DEVICE AND METHOD USING SAME

BACKGROUND OF THE INVENTION

1. Field of the Invention

The subject invention relates to a device for marking a tumor, breast lesion, or similar tissue mass of interest. Particularly, the subject invention is directed to a marker element to be positioned wholly within the body of a patient to prevent inadvertent displacement or removal of the marker element, as well as being directed to a localizing device using the same. An additional aspect of the subject invention includes a method for marking a tissue mass of interest using the marker element.

2. Description of Related Art

Interstitial medical diagnosis and treatment require means for effectively marking a tissue mass of interest, such as a tumor, lesion, cyst, or similar tissue disorder. Marking is conventionally accomplished using an elongate wire having a barbed or similarly engaging end. The elongate wire is configured to be inserted such that the barbed end penetrates the subject tissue mass with the opposite end of the elongate wire extending from the body so as to be visible upon inspection. In this manner, the elongate wire provides a path for subsequent incision and allows for easy removal of the wire once diagnosis and treatment are complete.

For example, U.S. Pat. No. 4,616,656 issued to Nicholson et al. is directed to the combination of a hollow probe sheath and a probe wire having a memory hook that is used for localizing small presymptomatic breast lesions. In general, the probe sheath and probe wire are inserted together into the body tissue and directed to the site of the lesion. Once properly positioned, the probe wire is pushed forward until a small curl or hook formed at its distal end anchors into the tissue at the lesion site. The probe sheath is then removed with the opposite end of the probe wire extending out of the body. A clamp member is mounted on the exposed end of the probe wire to further inhibit displacement. A similar localizing wire further including markers to establish the position of the surgeon's scalpel in relation to the barbed tip of the wire is disclosed in U.S. Pat. No. 5,158,084 to Ghiatas.

U.S. Pat. No. 5,059,197 (Urie et al.) likewise discloses a lesion localizing device including a graduated cannula having a pointed end and a wire that is bent at its distal end to form a flexible barb. The pointed end cannula is first inserted, in combination with a trocar, into the body and properly positioned. The trocar is them removed and the barbed wire is inserted into the pointed cannula to engage the body tissue. The flexible barb is specifically configured so as to prevent ingress or egress of the barbed wire, and the barbed wire is of sufficient length so as to extend from the body when fixed in position. During surgery, a second cannula having a blunt end is slid over the barbed wire for added strength.

The localizing needle assembly of U.S. Pat. No. 5,127,916 to Spenser et al. includes an outer tubular cannula and a needle structure slidingly mounted within the outer cannula. The needle structure includes a rearwardly extending retractable barb, and a non-retractable barb that is initially contained within the outer cannula. When positioning is satisfied, the outer cannula is removed such that both the retractable and non-retractable barbs engage the surrounding body tissue. The opposite end of the needle structure is configured to extend outside the body, and is reinforced for added strength. The needle structure apparently is removed during the surgical biopsy procedure.

Similarly, U.S. Pat. Nos. 4,774,948 and 4,931,059 to Markham each disclose an assembly including the combination of a hollow needle and a stylet having a barbed end for marking the location of tumors prior to surgery. The hollow needle is provided with one or more members to prevent over insertion of the assembly into the body tissue and to secure the needle against inadvertent movement when properly positioned. After the assembly is inserted into the body and located at the desired position, the stylet is drawn in a reverse direction until the barbed end extends from an opening provided in the hollow needle so as to engage the body tissue and secure the assembly in position. Throughout this operation, the opposite end of the hollow needle and stylet assembly remains exposed outside the body. When diagnosis and treatment are complete, the assembly is removed from the body tissue by first removing the stylet in a forward direction to urge its barbed end into the hollow needle so as to disengage the body tissue.

More recently, U.S. Pat. No. 5,396,897 was issued to Jain et al., which discloses a new method for localizing a lesion within a tissue mass. This method includes the initial step of inserting a hollow insertion needle into the patient. A sensor tube is located within the hollow insertion needle so as to detect a change in pressure, which corresponds to the location of the lesion. Once the location of the lesion is identified, the sensor tube is withdrawn and a conventional hook wire is inserted into the lumen of the insertion needle. The insertion needle is then likewise withdrawn so as to leave the hook wire implanted in the lesion as an accurate marker. The hook wire is of sufficient length so as to emerge from the location of insertion for the hollow needle and provide a guide for the surgeon's knife.

Rather than using a wire having a barbed or hooked end, U.S. Pat. No. 5,234,426 to Rank et al. discloses a marking wire having a helically wound coil end for localizing and marking lesions. The marking wire is inserted into a hollow needle and then rotated to anchor into the desired body tissue. The opposite end of the marking wire extends from the body and is provided with a similar helical coil, which cooperates with a guide device attached to the hollow needle to identify the depth of the marking wire when anchored.

Although these conventional devices and methods may be effective for marking a particular tissue mass, disadvantages have been identified. For example, because a conventional elongate wire extends outside of the body when in use, accidental impact with the exposed end of the elongate wire will likely dislodge the barbed or corkscrew end from the tissue mass of interest as well as cause unnecessary trauma to the surrounding body tissue.

Additionally, recent developments in the diagnosis and laser treatment of lesions, particularly located in the breast, have created a need for a marker that can remain within the body even after treatment to allow future observation and monitoring of the treated area. Conventional elongate wires, however, must be removed upon completion of the interstitial treatment such that no marker remains to assist in such observation. The subject invention addresses the disadvantages of these conventional marking devices and methods.

SUMMARY OF THE INVENTION

The purpose and advantages of the invention will be set forth in and apparent from the description and drawings that follow, as well as will be learned by practice of the invention. Additional advantages of the invention will be realized and attained by the elements of the apparatus and method particularly pointed out in the appended claims.

To achieve these and other advantages and in accordance with the purpose of the invention, as embodied and broadly described herein, a marker element is provided to be positioned wholly within the body of a patient using a guide member having a guide path so as to mark a tissue mass of interest. The marker element of the subject invention generally includes a resilient member capable of collapsing to a reduced size for movement along the guide path of the guide member, yet substantially resuming its original shape and size upon discharge from the guide member so as to remain in a fixed position wholly within the body without irritating or traumatizing the surrounding tissue. To allow localization and monitoring without surgical incision, and further in accordance with the subject invention, the marker element is made of radiopaque material. The term "radiopaque material" as used herein is understood to include any material capable of being detected using conventional radiographic, sonographic, thermographic, or magnetic techniques.

Preferably, the resilient member of the marker element includes at least two leg portions of approximately equal length that are connected at an angle relative to each other so as to form a generally V-shape. When introduced into the guide path of the guide member, such as the lumen of a cannula, the leg portions shift toward each other to facilitate easier movement of the resilient member. When discharged from the cannula wholly within the body, the resilient member substantially resumes its original V-shape so as to lodge in the desired position proximate the tissue mass of interest.

The subject invention likewise includes a localizing device using the marker element described above for marking a tissue mass of interest within the body of a patient. In addition to the marker element, the localizing device includes an elongate guide member having a first end to be inserted into the body so as to be directed toward a position proximate the tissue mass and an opposite second end to extend from the body after the first end has been inserted therein. A guide path extends between the first end and the second end of the guide member. Preferably, the guide member is a hollow cannula having a funnel-shaped second end.

A marker element dispenser is provided to engage the funnel-shaped second end and simplify introduction of a marker element into the guide path of the guide member. The marker element dispenser preferably includes a plunger assembly and a track that supports a plurality of marker elements. Once introduced, the marker element is urged along the guide path of the guide member using a prodding member so as to discharge the marker element from the first end of the guide member wholly within the body such that the marker element is positioned proximate the tissue mass.

The objects and advantages of the subject invention are further achieved by a method for marking a tissue mass of interest within the body of a patient. The method includes the steps of identifying the tissue mass of interest; inserting the elongate guide member described above into the body of the patient such that the first end of the elongate guide member is directed toward a position proximate the tissue mass and the opposite end of the guide member extends from the body; introducing the marker element described above into the second end of the guide member; and then urging the marker element along the guide path from the second end of the guide member to the first end. In this manner, the marker element is discharged from the first end of the guide member and positioned wholly within the body proximate the tissue mass of interest. The method further includes removing the guide member from the body with the marker element remaining wholly within the body positioned proximate the tissue mass, and repeating the above steps if a plurality of marker elements are desired to mark the tissue mass of interest.

It is to be understood that both the foregoing general description and the following detailed description are exemplary and provided for purpose of explanation only, and are not restrictive of the invention, as claimed.

BRIEF DESCRIPTION OF THE DRAWINGS

The accompanying drawings, which are incorporated in and constitute a part of this specification, illustrate the preferred embodiment of the invention, and together with the description, serve to explain the principles of the invention.

FIG. 6A is a cross-sectional side elevation view of a schematic representation of a marker element dispenser of the subject invention.

FIG. 6B is a cross-sectional front elevation view of a schematic representation of the marker element dispenser shown in FIG. 6A.

FIG. 7A is a schematic representation of a guide member and prodding member being inserted into the body of a patient in accordance with the method of the subject invention.

FIG. 7B is a schematic representation of a marker element being introduced into the guide member of FIG. 7A using a marker element dispenser in accordance with the method of the subject invention.

DETAILED DESCRIPTION OF THE PREFERRED EMBODIMENT

Figure 1B:
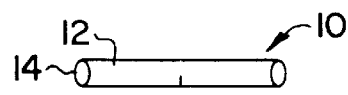
FIG. 1B is a top plan view of the marker element shown in FIG. 1A.

Reference will now be made in detail to the present preferred embodiment of the subject invention, examples of which are illustrated in the accompanying drawings. Wherever possible, the same reference characters will be used throughout the drawings to refer to the same or like parts. The method of the subject invention will be described in conjunction with the marker element and localizing device for clarity.

In accordance with the subject invention, a marker element is provided for marking a tumor, lesion, cyst, or similar tissue mass of interest for diagnosis and treatment. The marker element of the subject invention is particularly configured to be positioned wholly within the body of the patient proximate the tissue mass of interest. In this manner, the risk of displacement of the marker element and trauma to the surrounding tissue is minimized because the marker element does not include any portions exposed outside the body after insertion. By positioning the marker element wholly within the body, the marker element of the subject invention likewise may be used for subsequent observation and monitoring of the tissue mass of interest and surrounding area.

Generally, the marker element of the subject invention is positioned wholly within the body of the patient using a guide member having a guide path extending therethrough as described in detail below. The marker element embodied herein therefore is a resilient member capable of collapsing to a reduced size for movement along the guide path of the guide member, yet substantially resuming its original shape and size upon discharge from the guide member so as to remain in a fixed position within the body without irritating or traumatizing the surrounding tissue. To allow localizing and monitoring without surgical incision, and further in accordance with the subject invention, the marker element is made of radiopaque material. The term "radiopaque material" as used herein is understood to include any material capable of being detected using conventional radiographic, sonographic, thermographic, or magnetic techniques.

For purpose of illustration and not limitation, three (3) exemplary embodiments of the marker element of the subject invention are shown in FIGS. 1A through 3B and designated generally by reference character 10. In each of these three embodiments, the marker element 10 includes a resilient member having a generally V-shape. These figures show that each of the resilient members embodied herein preferably includes at least two (2) leg portions 12 of approximately equal length connected at an angle relative to each other. The apex 16 at which the leg portions 12 are connected defines the forward end of the marker element 10. In this manner, the resilient member is capable of at least partially collapsing such that the leg portions 12 shift toward each other when urged through a constricted area, such as the lumen of a cannula, and then substantially resuming its original V-shape upon discharge from the constricted area.

Figure 2B:
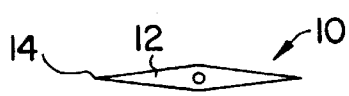
FIG. 2B is a top plan view of the marker element shown in FIG. 2A.
Figure 1A:
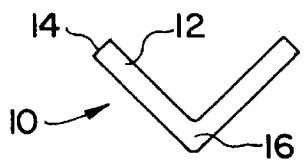
FIG. 1A is an enlarged front elevation view of a representative embodiment of the marker element of the subject invention.
Figure 2A:
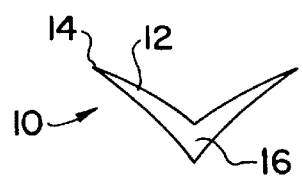
FIG. 2A is an enlarged front elevation view of another representative embodiment of the marker element of the subject invention.

Particularly, the marker element 10 embodied in FIGS. 1A–1B includes two (2) coplanar leg portions 12 of approximately equal length connected at an angle between about 20° and 90° relative to each other, with a preferred range between about 30° and 45°. Each leg portion 12 of this embodiment is generally straight and includes a blunt distal end 14. As will be described, these distal ends 14 provide a surface against which a prodding member can engage and assist in preventing rearward movement of the marker element 10 once positioned within the body. The marker element 10 embodied in FIGS. 2A–2B is similar to that of FIGS. 1A–1B; however, each leg portion 12 of this embodiment is generally arcuate and provided with a tapered distal end 14. The leg portions 12 of this configuration therefore have an enhanced tendency to spread outwardly from each other during rearward movement, thus likewise inhibiting rearward movement.

Figure 3B:
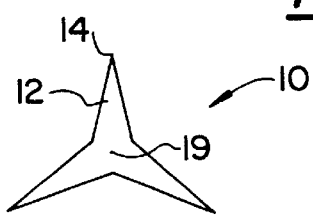
FIG. 3B is a top plan view of the marker element shown in FIG. 3A.
Figure 3A:
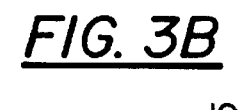
FIG. 3A is an enlarged front elevation view of another representative embodiment of the marker element of the subject invention.

Unlike the previous two embodiments, the marker element 10 of FIGS. 3A–3B includes three (3) centrally-connected leg portions 12 of approximately equal length. These three leg portions 12 preferably are spaced equally, i.e., 120° from each other, around the central axis 19 of the marker element 10 as shown in FIG. 3B. Likewise, each leg portion 12 extends from the central axis 19 of the marker element 10 at an angle α between about 10° and 45°, with a preferred range of about 15° and 25°, as shown in FIG. 3A. Although FIGS. 3A–3B show leg portions 12 configured similar to that of the embodiment of FIGS. 2A–2B, which are arcuate with tapered distal ends 14, this embodiment of the marker element 10 likewise may include leg portions 12 that are straight, or leg portions 12 provided with blunt ends, or a combination thereof. Additionally, the marker element 10 may include four or more leg portions if desired and appropriately sized.

In each embodiment of the marker element 10, the leg portions 12 preferably are between about 3 mm and 6 mm in length, although a length of about 5 mm is preferred. The apex 16 may be rounded or brought to a point as shown. Additionally, the distal end 14 of each leg portion 12 may include a barb or similar extension, as shown in U.S. Pat. Nos. 4,774,948, 4,931,059, and 5,127,916, to inhibit or prevent movement of the marker element 10 once positioned in the body tissue.

As noted above, the marker element 10 of the subject invention is made of radiopaque material such as stainless steel or the like. For simplicity and reduced costs, the marker element 10 preferably is constructed as a single piece element using conventional machining techniques; however, welding or similar construction methods may be used to assemble the marker element 10 from two or more pieces if desired. Particularly, the coplanar configuration of the marker elements 10 embodied in FIGS. 1A–2B allows for simplified construction and minimized costs.

Although reference is made to a marker element having two or more centrally-connected leg portions that form a generally V-shaped resilient member, alternative configurations of the marker element likewise may be used. For example, a solid member made of suitable resilient material may be used, provided that the member is capable of collapsing or being compressed to an appropriate size to move along the guide path or a guide member, yet resuming a sufficient configuration upon discharge from the guide member to remain in a substantially fixed position wholly within the body without irritating or traumatizing the surrounding tissue. Such a marker element would have a triangular or pyramidal configuration when not compressed.

The marker element of the subject invention may be positioned wholly within the body of a patient by employing a variety of methods. In accordance with another aspect of the subject invention, however, a localizing device is provided to minimize scarring and trauma incurred by the patient as well as to reduce the risks and expenses associated with conventional techniques. The localizing device 100 of the subject invention includes an elongate guide member 20 having a first end 22 to be inserted into the body so as to be directed toward a position proximate the tissue mass of interest, and an opposite second end 24 configured to extend from the body. The guide member 20 therefore is of sufficient length to allow the opposite second end 24 of the guide member 20 to extend from and be exposed outside the body when the first end 22 is properly inserted. The guide member 20 further includes a guide path 26 extending between the second end 24 and the first end 22 for implanting and positioning a marker element 10 wholly within the body, as will be described. Additionally, the guide member 20 is configured to be removed from the body after the marker element 10 has been positioned proximate the tissue mass as will be described.

Figure 4:
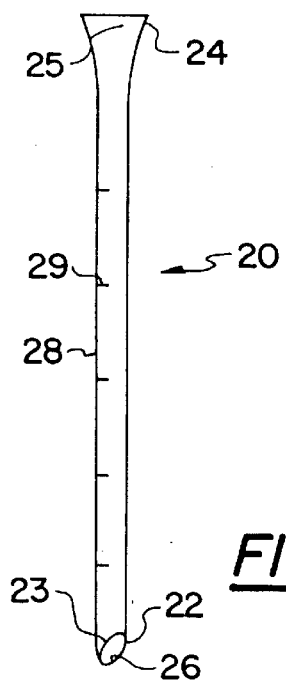
FIG. 4 is a front elevation view of a representative embodiment of the guide member of the subject invention.

FIG. 4 shows one embodiment of a guide member 20 provided in accordance with the subject invention, although alternative configurations and constructions may be used. The guide member 20 includes a hollow cannula having a first end 22 configured for insertion into the body of a patient. For example, FIG. 4 shows that the first end 22 preferably is beveled or angled to form a cutting edge 23, although alternative configurations of the first end 22 may be provided. The cannula 20 therefore is capable not only of insertion into a body cavity, but also penetration of tissue structure for insertion into a tissue mass. This configuration of the first end 22 likewise allows the guide member 20 to be appropriately moved or repositioned within the body, such that the first end 22 may be directed toward the tissue mass of interest. This is accomplished in combination with conventional medical imaging technology so as to identify the location of the tissue mass of interest, as well as the location and direction of the first end 22 of the guide member 20 relative thereto.

The second end 24 of the guide member 20 embodied in FIG. 4 is preferably provided with a funnel shape 25 so as to simplify the introduction of marker elements 10 into the guide member 20. The funnel shape 25 of the second end 24 not only receives the marker element 10 more readily, but also may be used to support the marker element 10 until the physician is prepared to urge the marker element 10 into position. Additionally, and as described below, the funnel shape 25 of the second end 24 likewise may be used to engage and support a marker element dispenser to further simplify the introduction of marker elements 10.

The lumen of the cannula 20, which extends from the second end 24 to the first end 22, forms the guide path 26 of the guide member 20. The marker element 10 that is introduced into and supported by the second end 24 of the guide member 20 therefore can be urged down the guide path or lumen 26 toward the first end 22 of the guide member 20 until the marker element 10 is positioned wholly within the body proximate the tissue mass of interest as described further below. If desired, a track or set of grooves corresponding to the distal ends 14 of the leg portions 12 may be provided along the length of the guide path 26 to further assist in alignment of the marker element 10.

FIG. 4 also shows that the guide member 20 is provided with a substantially smooth outer surface 28. This configuration allows easy removal of the guide member 20 from the body once the marker element 10 is properly positioned proximate the tissue mass of interest. Markings or similar indicia 29 may be provided on the outer surface 28 of the guide member 20, however, to indicate the depth of insertion and assist in positioning the guide member 20.

The appropriate size and construction of the guide member 20 shown in FIG. 4 will depend upon the intended use and application. For example, a guide member 20 used in conjunction with the marker element 10 of the subject invention for marking a breast lesion would have a guide path 26 between about 15 cm and 25 cm long, with a preferred length of about 20 cm. The cross dimension of the guide path 26 would be between about 20 gauge (0.9 mm) and 18 gauge (1.2 mm), and the cross dimension at the mouth of the second end 24 would be between about 7 mm and 10 mm. The guide member 20 preferably is made of stainless steel or a similar material using conventional manufacturing techniques.

To introduce the marker element into the second end of the guide member after the guide member has been inserted into the body of the patient, conventional instruments may be used. This process is simplified, however, by using a marker element dispenser in accordance with another aspect of the invention. The marker element dispenser is configured to engage readily the second end of the guide member such that a marker element can be easily dispensed from the marker element dispenser directly into the second end of the guide member.

FIGS. 6A and 6B show a schematic representation of a marker element dispenser in accordance with the subject invention. The marker element dispenser 50 generally includes a housing 52 containing at least one marker element 10. The marker element 10 is dispensed from the housing 52 through an aperture 55 formed in a lower portion thereof. The housing 52 preferably includes an extension 54 provided proximate the aperture 55 and configured to engage the second end 24 of the guide member 20, as shown in FIG. 7B. If desired, a snap-fit connection or similar attachment arrangement may be provided to temporarily secure the marker element dispenser 50 and guide member 20 together. With the extension 54 engaging the second end 24 of the guide member 20, the marker element 10 may be introduced directly into the guide member 20 when dispensed from the marker element dispenser 50. Alternatively, the extension 54 may be provided separately as an adaptor between the marker element dispenser 50 and the second end 24 of the guide member 20.

The marker element dispenser 50 shown in FIGS. 6A and 6B further includes a plunger assembly 60 having an elongate stem portion 62 aligned with the aperture 55. When the plunger assembly 60 is actuated, the stem portion 62 is moved from a retracted position to an extended position. In this manner, the marker element 10 aligned with the elongate stem portion 62 is forced through the aperture 55 and dispensed from the housing 52. Preferably, the stem portion 62 has a first end 63 configured to abut the distal ends 14 of the marker element 10, an opposite end 65 having an actuation pad 64, and an overall length sufficient to force the marker element 10 through the aperture 55 and into the guide path 26 beyond the funnel shape 25 of the guide member 20 as schematically shown in FIG. 7B. It is further preferred that the plunger assembly 60 is biased by a spring 66 or similar resilient member so as to return the stem portion 62 to the retracted position after actuation. In lieu of the plunger assembly, a second aperture may be provided through the housing 52 in line with the first aperture 55 so as to receive a prodding member or similar structure and allow the marker element 10 to be formed through the first aperture 55.

The marker element dispenser 50 may contain only one marker element 10 for a single use or, as shown in FIGS. 6A and 6B, may contain a plurality of marker elements 10. In this embodiment, a track 56 is provided extending between a first end 51 and a second end 53 of the housing 52. The track 56 is configured to support one or more marker elements 10; preferably with the marker elements 10 maintained in a collapsed condition as shown in FIG. 6B. With the aperture 55 and plunger assembly 60 located at the first end 51 of the housing 52, as shown in FIG. 6A, a biasing device 58 is provided at the second end 53 of the housing 52 to sequentially advance the remaining marker elements 10 toward the aperture 55. In this manner, a single marker element dispenser may be used repeatedly, thus reducing costs and potential delays during the localizing procedure.

The various components of the marker element dispenser 50 preferably are constructed of a light-weight, durable material such as plastic. Although the housing 52 may be constructed to allow replacement of marker elements 10 for additional use, it is preferred that the housing 52 is sealed so as to be disposed of after all of the marker elements 10 are dispensed therefrom. The dimensions and overall design of the marker element dispenser 50 will depend upon the dimensions of the marker elements 10, as well as the number of marker elements 10 to be contained within the housing 52.

Once introduced into the second end 24 of the guide member 20, and as mentioned above, the at least partially collapsed marker element 10 is urged along the guide path 26 so as to be discharged from the first end 22 of the guide member 20 wholly within the body of the patient where the marker element resumes its generally V-shaped configuration. The urging and discharge are accomplished using a prodding member 30, such as a stylet or similar elongate structure appropriately sized to fit inside the guide path or lumen 26 of the cannula 20 with the marker element 10. One embodiment of such a prodding member 30 is shown in FIG. 5.

The prodding member 30 has a length greater than that of the guide member 20, and a cross-sectional dimension substantially equal to or smaller than that of the guide path 26. The prodding member 30 also includes a straight or beveled end 32 capable of engaging and pushing against the distal ends 14 of the leg portions 12, which are collapsed within the guide path or lumen 26. By forming the prodding member 30 as a solid member with a beveled end 32 that is angled similar to that of the first end 22 of the guide member 20, the prodding member 30 likewise may be used as a trocar during insertion of the guide member 20. As with the guide member 20, the prodding member 30 preferably is made of stainless steel or similar material.

Figure 5:
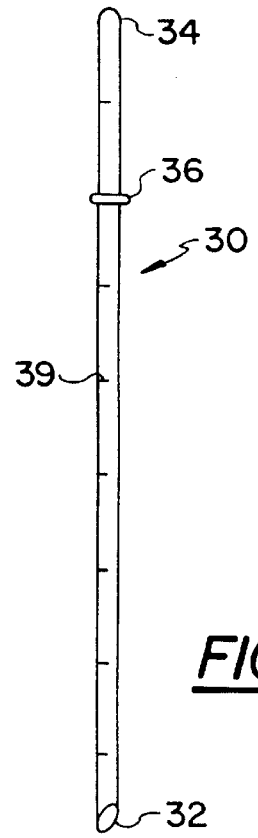
FIG. 5 is a front elevation view of a representative embodiment of the prodding member of the subject invention.

The opposite end 34 of the prodding member 30 may be contoured so as to receive the fingers of the physician comfortably, or may be smooth as shown in FIG. 5 to simplify and reduce costs of construction. Markings or similar indicia 39 may be provided on the prodding member 30 to indicate the location of the end 32, and thus the marker element 10, relative to the guide member 20. Likewise, an additional step, protrusion, or similar indicia 36 may be provided on the prodding member 30 to indicate that the beveled end 32 of the prodding member 30 is aligned with the first end 22 of the guide member 20 to prevent the prodding member 30 from being inserted further.

For purpose of illustration and not limitation, reference is now made to a method of using the marker element 10 and localizing device 100 of the subject invention. Particularly, FIGS. 7A–7G sequentially depict various steps of the method preformed in accordance with the subject invention. Although the method schematically shown in FIGS. 7A–7G uses the marker element 10 of FIGS. 2A–2B and the guide member 20 of FIG. 4, as shown in cross-section, it is understood that the method described herein likewise may use any alternative embodiment of the marker element 10 and guide member 20 if desired. It is further noted that the schematic representations of FIGS. 7A–7G are not presented to scale.

The marker element 10 and localizing device 100 of the subject invention may be used to mark a tissue mass of interest for subsequent diagnosis, treatment, and observation. Examples of such tissue masses include tumors, lesions, cysts, and other tissue disorders. Therefore, the tissue mass of interest initially must be identified. This is performed using conventional radiographic, sonographic, thermographic, or magnetic imaging techniques. Preferably, coordinates identifying the actual location of the tissue mass are determined using stereotaxic techniques or the like. These coordinates then may be used to assist in properly positioning the marker element 10 accordingly. Alternatively, it is sufficient to identify the tissue mass of interest using conventional imaging techniques, and then guide and adjust the placement of the marker element 10 either in real time or using subsequent images.

One the tissue mass of interest is identified, the elongate guide member 20 described above is inserted into the body of the patient. That is, the guide member 20 is penetrated into and inserted through the body tissue until the first end 22 of the elongate guide member 20 is directed toward a desired position proximate the tissue mass while the opposite second end 24 of the guide member 20 remains extending from the body as shown in FIG. 7A. If the actual coordinates of the tissue mass of interest are known, the orientation and depth of insertion of the guide member 20 can be calculated readily such that the guide member 20 can be properly inserted in a single step. The coordinates can be established and the guide member directed by using a stereotaxic table. If not know, the guide member 20 can be inserted into the general area of the tissue mass of interest, and then guided to the desired position using conventional imaging techniques.

As noted above, the guide member 20 of the subject invention includes a guide path 26 extending from the second end 24 to the first end 22. Preferably, the prodding member 30 or a similar solid member is located in the guide path 26 during insertion of the guide member 20 with the beveled ends 22, 32 substantially aligned to inhibit or prevent body tissue from entering therein. The prodding member 30 thus substantially blocks the guide path 26 and simplifies insertion of the guide member 20. Additionally, it is possible that the prodding member 30 may be used to ensure proper placement of the guide member 20 prior to positioning of the marker element 10. This may be accomplished by moving the prodding member 30 forward so as to expose the beveled end 32 of the prodding member 30 beyond the first end 22 of the guide member 20. If the beveled end 32 of the prodding member 30 does not extend through the desired position of the marker, the guide member 20 is redirected accordingly.

The method of the subject invention also includes the step of introducing a marker element 10 into the second end 24 of the guide member 20. The marker element 10 embodied herein is a resilient member capable of collapsing to a reduced size and then substantially resuming its original shape and size. As noted above, this step is simplified by providing the second end 24 of the guide member 20 with a funnel shape 25 so as to readily receive and support the marker element 10. Although the marker element 10 may be introduced manually using conventional equipment, this step is even further simplified by using a marker element dispenser 50 as shown in FIG. 7B.

Figure 7C:
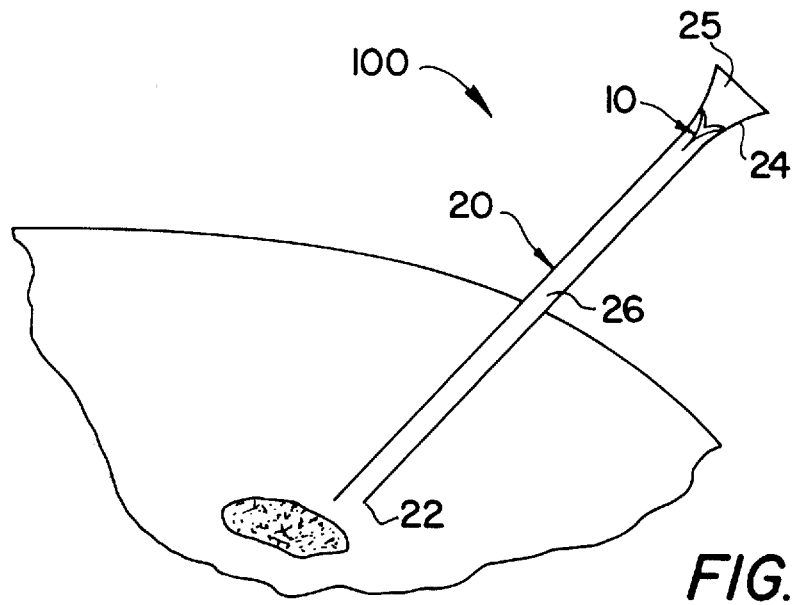
FIG. 7C is a schematic representation of a marker element introduced in the guide member of FIG. 7B in accordance with the method of the subject invention.

With the guide member 20 properly inserted into the body and the prodding member 30 removed, the marker element dispenser 50 is engaged with the second end 24 of the guide member 20. The plunger assembly 60 is actuated using the actuation pad 64, such that the stem portion 62 forces a marker element 10 through the aperture 55 and into the guide path 26 beyond the funnel shape 25 of the guide member 20. Upon release of the actuation pad 64, the stem portion 62 returns to its retracted position and the next marker element 10 that is supported on the track 56 is sequentially advanced into alignment with the aperture 55. The marker element dispenser 50 is then removed for later use as shown in FIG. 7C.

Figure 7D:
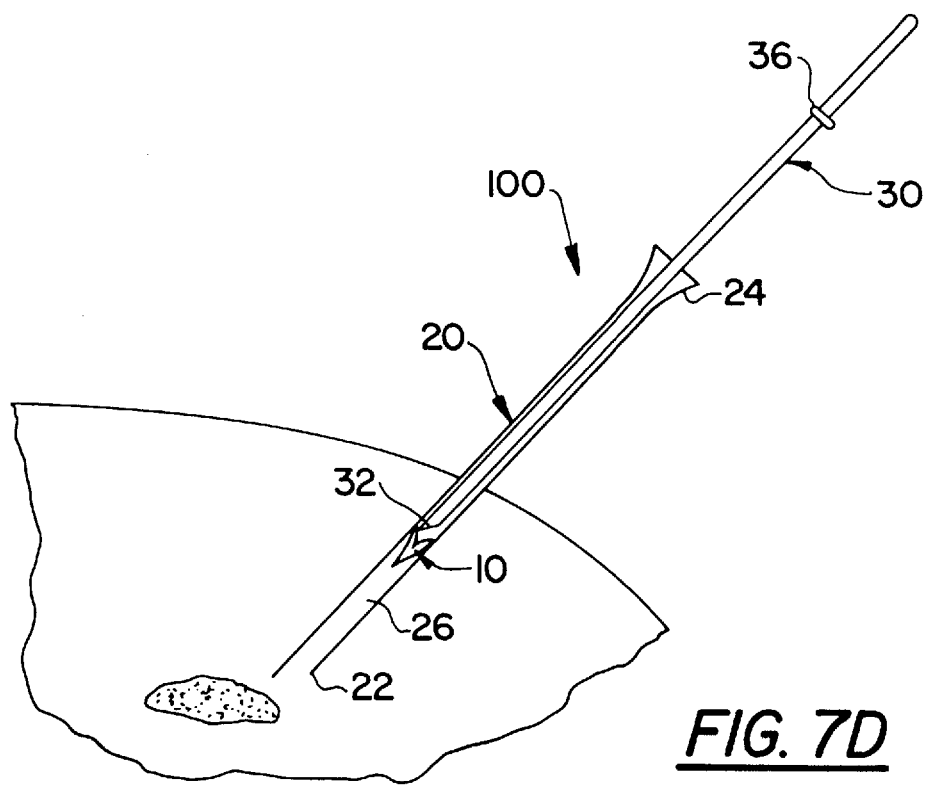
FIG. 7D is a schematic representation of a marker element being urged along the guide member of FIG. 7C toward a tissue mass of interest in accordance with the method of the subject invention.

The marker element 10 that is introduced into the second end 24 of the guide member 20 is then urged along the guide path 26 toward the first end 22. This step preferably is accomplished using the prodding member 30. During the urging step, the resilient member collapses and remains collapsed during movement along the guide path 26 of the guide member 20. For example, when a substantially V-shaped marker element 10 is used, the leg portions 12 of the resilient member shift toward each other. The beveled end 32 of the prodding member 30 therefore engages the distal ends 14 of the marker element 10 to urge the marker element 10 through the constricted area of the guide path 26 as shown in FIG. 7D.

Figure 7E:
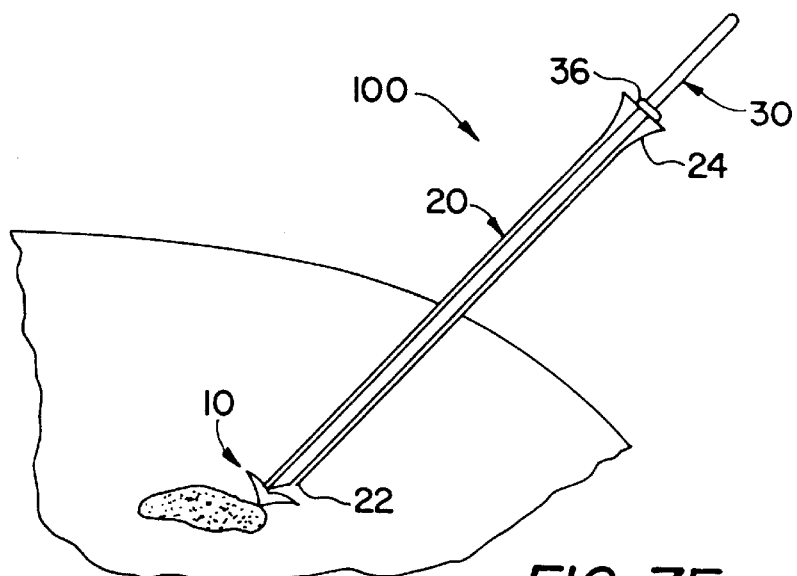
FIG. 7E is a schematic representation of the marker element of FIG. 7D being positioned proximate the tissue mass of interest in accordance with the method of the subject invention.
Figure 7F:
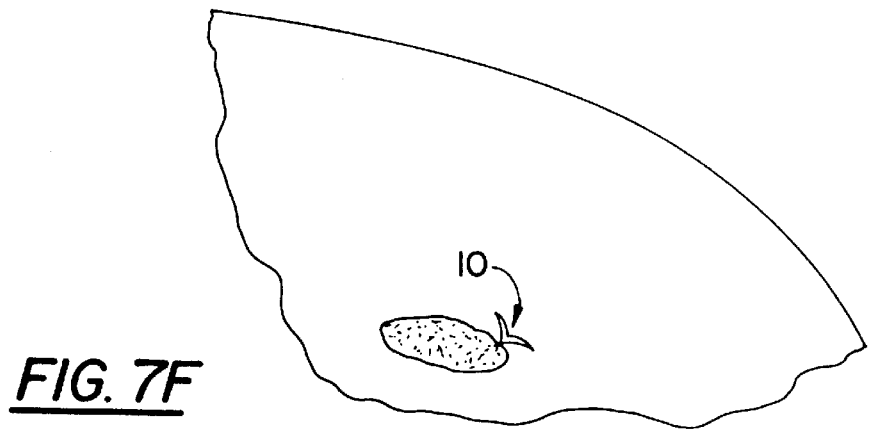
FIG. 7F is a schematic representation of the marker element of FIG. 7E positioned proximate the tissue mass of interest with the guide member and prodding member removed in accordance with the method of the subject invention.

The urging step is continued until the marker element 10 is discharged from the first end 22 of the guide member 20 wholly within the body as shown in FIG. 7E. Upon discharge from the first end 22 of the guide member 20, the marker element 10 substantially resumes its original shape and size so as to remain in a fixed position within the body without irritating or traumatizing the surrounding tissue. By properly inserting the guide member 20 prior to urging the marker element 10 therethrough, the marker element 10 is readily positioned proximate the tissue mass of interest as desired upon discharge from the first end 22 of the guide member 20. Because the marker element 10 is made of radiopaque material, its position can be verified using conventional imaging techniques. The guide member 20 and prodding member 30 are then easily removed with the marker element 10 remaining wholly within the body positioned proximate the tissue mass of interest as shown in FIG. 7F.

Figure 7G:
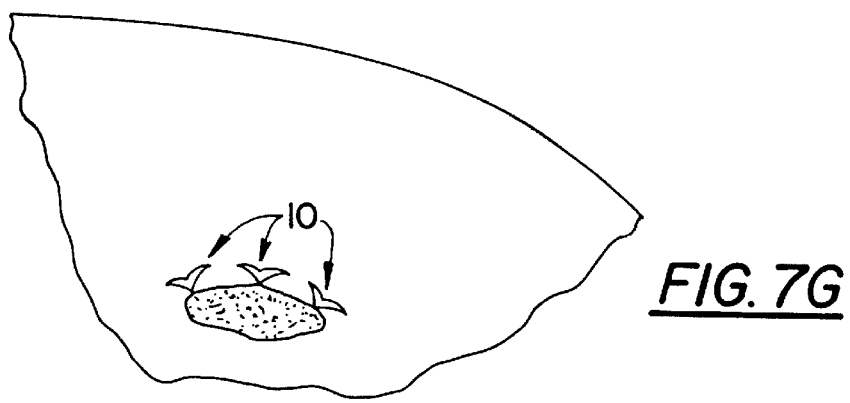
FIG. 7G is a schematic representation of a plurality of marker elements positioned proximate the tissue mass of interest in accordance with the method of the subject invention.

Generally, the use of one marker element 10 of the subject invention will be sufficient to mark a tissue mass of interest. It is possible, however, that two or more marker elements 10 may be desired or required to adequately mark a tissue mass of relatively large size as shown in FIG. 7G. This is accomplished by repositioning the guide member 20 such that the first end 22 of the elongate guide member 20 is directed toward another position proximate the tissue mass, and then repeating the remaining steps of the method described above accordingly. That is, a second marker element 10 is introduced into the second end 24 of the guide member 20 and then urged along the guide path 26 of the guide member 20 from the second end 24 to the first end 22 so as to discharge from the first end 22 of the guide member 20 wholly within the body. Upon discharge, the second marker element 10 is positioned in a second position proximate the tissue mass of interest and the guide member 20 is removed.

In view of the description above, it is evident that a marker element of the subject invention may be positioned wholly within the body of a patient proximate a tissue mass of interest. The marker element, as well as all components of the invention, may be sterilized in a manner known for surgical devices. The marker elements are configured to remain wholly within the body without irritating or traumatizing the surrounding tissue. In this manner, these marker elements are unexposed so as not to become displaced or dislodged by inadvertent impact, and may remain within the body even after treatment is completed to allow subsequent identification and observation of the marked area. If desired, these marker elements likewise may be removed readily using conventional surgical techniques.

The marker elements of the subject invention, as well as the localizing device and method using the same, maybe used in conjunction with a variety of conventional medical procedures. However, the subject invention is particularly suited for orthoscopic and interstitial diagnostic and treatment techniques. For example, U.S. Pat. Nos. 5,169,396 and 5,222,953 disclose a method and apparatus for interstitial laser therapy for non-contact treatment of solid tumors in various organs. The marker elements as well as the localizing device and method of the subject invention therefore may be used for marking the solid tumor to be treated by the method and apparatus of these patents and to allow subsequent identification and observation of the treated area.

Although reference has been made to specific embodiments of the subject invention for purpose of explanation, it is understood that alternative configurations and methods are possible. It also will be apparent to those skilled in the art that various modifications and variations can be made in the design and construction of the marker element and localizing device, as well as in the performance of the method, without departing from the scope or spirit of the invention. Each patent cited herein is hereby incorporated by reference in its entirety and relied upon.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A localizing device for marking a tissue mass of interest within the body of a patient, the localizing device comprising:

a) an elongate guide member having a first end to be inserted into the body so as to be directed toward a position proximate the tissue mass and an opposite second end to extend from the body after the first end has been inserted therein, the guide member including a guide path extending between the first end and the second end;

b) at least one marker element to be positioned wholly within the body proximate the tissue mass by introducing the marker element into the second end of the guide member and discharging the marker element from the first end of the guide member, wherein said marker element has a resilient member; and c) a prodding member to urge the marker element along the guide path of the guide member from the second end to the first end so as to discharge the marker element from the first end of the guide member wholly within the body such that the marker element is positioned proximate the tissue mass.

2. The localizing device of claim 1, wherein the guide member is a hollow cannula.

3. The localizing device of claim 2, wherein the second end of the guide member is funnel-shaped.

4. The localizing device of claim 1, wherein the marker element is made of radiopaque material.

5. The localizing device of claim 4, wherein the radiopaque material is stainless steel.

6. The localizing device of claim 1, wherein the resilient member has a V-shape configured to collapse during movement along the guide member and to resume the V-shape upon discharge from the first end of the guide member.

7. The localizing device of claim 1 further comprising a marker element dispenser to introduce the marker element into the second end of the guide member.

8. The localizing device of claim 7, wherein the marker element dispenser includes a plunger assembly to force the marker element into the guide path of the guide member.

9. The localizing device of claim 7, wherein the marker element dispenser includes a track supporting a plurality of marker elements.

10. A marker element to be positioned wholly within the body of a patient using a hollow cannula to mark a tissue mass of interest therein, the marker element comprising:

a resilient member including at least two leg portions of equal length connected at an angle to each other to form a V-shape, the resilient member configured to collapse when introduced into the cannula such that the at least two leg portions shift toward each other to allow movement of the resilient member through the cannula, the resilient member further configured to resume the V-shape upon discharge from the cannula so as to be positioned wholly within the body proximate the tissue mass.

11. The marker element of claim 10, wherein the resilient member is made of radiopaque material.

12. A method for marking a tissue mass of interest within the body of a patient, the method comprising the steps of:

a) identifying the tissue mass of interest;

b) inserting an elongate guide member into the body of the patient such that a first end of the guide member is directed toward a position proximate the tissue mass and an opposite second end of the guide member extends from the body after the first end has been inserted therein, the guide member including a guide path extending between the first end and the second end;

c) introducing a marker element into the second end of the guide member, wherein said marker element has a resilient member;

d) urging the marker element along the guide path of the guide member from the second end to the first end so as to discharge the marker element from the first end of the guide member wholly within the body such that the marker element is positioned proximate the tissue mass; and e) removing the guide member from the body with the marker element remaining wholly within the body positioned proximate the tissue mass.

13. The method of claim 12, wherein the guide member inserted during the inserting step is a hollow cannula.

14. The method of claim 12, wherein the introducing step includes engaging a marker element dispenser with the second end of the guide member and dispensing the marker element therefrom into the guide path of the guide member.

15. The method of claim 12, wherein the marker element introduced during the introducing step is made of a radiopaque material.

16. The method of claim 12, wherein the resilient member has a V-shape.

17. The method of claim 16, wherein during the urging step, the resilient member is at least partially collapsed during movement along the guide member and resumes the V-shape upon discharge from the first end of the guide member.

18. The method of claim 12, wherein the urging step includes pushing the marker element along the guide path of the guide member from the second end to the first end using a prodding member.

19. A method for marking a tissue mass of interest within the body of a patient, the method comprising the steps of:

a) identifying the tissue mass of interest;

b) inserting an elongate guide member into the body of the patient such that a first end of the guide member is directed toward a position proximate the tissue mass and an opposite second end of the guide member extends from the body after the first end has been inserted therein, the guide member including a guide path extending between the first end and the second end;

c) introducing a marker element into the second end of the guide member, wherein said marker element has a resilient member;

d) urging the marker element along the guide path of the guide member from the second end to the first end so as to discharge the marker element from the first end of the guide member wholly within the body such that the marker element is positioned proximate the tissue mass;

e) repositioning the guide member such that the first end of the guide member is directed toward another position proximate the tissue mass;

f) introducing an additional marker element into the second end of the guide member;

g) urging the additional marker element along the guide path of the guide member from the second end to the first end so as to discharge the additional marker element from the first end of the guide member wholly within the body such that the additional marker element is positioned in an additional position proximate the tissue mass; and h) removing the guide member from the body with the marker elements remaining wholly within the body positioned proximate the tissue mass.

20. The method of claim 19, further comprising the step of:

i) repeating steps e), f) and g) at least one time.

* * * * *